United States Patent [19]

Doria et al.

[11] Patent Number: 4,490,376
[45] Date of Patent: Dec. 25, 1984

[54] SUBSTITUTED ETHENYL DERIVATIVES OF 1H-PYRAZOLO-[1,5-A]PYRIMIDINE HAVING GASTROENTERIC ACTIVITY, COMPOSITIONS THEREOF, AND METHODS OF USING THE SAME

[75] Inventors: Gianfederico Doria, Milan; Carlo Passarotti, Gallarate; Giuliana Arcari, Milan, all of Italy

[73] Assignee: Farmitalia Carlo Erba S.p.A, Milan, Italy

[21] Appl. No.: 474,887

[22] Filed: Mar. 14, 1983

[30] Foreign Application Priority Data

Mar. 25, 1982 [GB] United Kingdom ............... 8208763

[51] Int. Cl.$^3$ ............... C07D 487/04; A61K 31/505
[52] U.S. Cl. ............................. 424/251; 544/281
[58] Field of Search ...................... 544/281; 424/251

[56] References Cited

U.S. PATENT DOCUMENTS

| | | | |
|---|---|---|---|
| 3,907,799 | 9/1975 | O'Brien et al. | 544/281 |
| 3,920,652 | 11/1975 | Springer et al. | 544/281 |
| 3,925,385 | 12/1975 | O'Brien et al. | 544/281 |
| 4,093,617 | 6/1978 | Robins et al. | 544/281 |
| 4,129,738 | 12/1978 | Hoehn | 544/281 |
| 4,281,000 | 7/1981 | Dusza et al. | 544/281 |

FOREIGN PATENT DOCUMENTS 18455 6/1970 Japan ........................ 544/281

OTHER PUBLICATIONS

Derwent Abstract of Japanese Patent Application 14424/66.
Derwent Abstract of Belgian Patent 847698.
Derwent Abstract of Dutch Patent 72-11011.

*Primary Examiner*—Robert Gerstl
*Assistant Examiner*—S. A. Gibson
*Attorney, Agent, or Firm*—Murray, Whisenhunt and Ferguson

[57] ABSTRACT

Compounds of the formula (I)

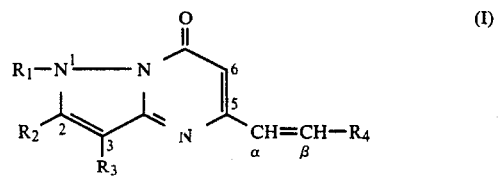

wherein
$R_1$ is:
(a) hydrogen, or $C_1$-$C_6$ alkyl;
(b) an unsubstituted 2-pyridyl or 3-pyridyl group;
(c) a benzyl group, wherein the phenyl ring is unsubstituted or substituted by halogen, $C_1$-$C_6$ alkoxy or $C_1$-$C_6$ alkyl;
(d) a phenyl ring, unsubstituted or substituted by one or two groups chosen from halogen, trihalomethyl, $C_1$-$C_6$ alkoxy, $C_1$-$C_6$ alkyl, $C_2$-$C_6$ alkanoylamino, nitro and amino;
each of $R_2$ and $R_3$ independently represents hydrogen, halogen or $C_1$-$C_6$ alkyl;
$R_4$ represents a 2-pyridyl, 3-pyridyl or 4-pyridyl group, unsubstituted or substituted by $C_1$-$C_6$ alkyl;
and the pharmaceutically acceptable salts thereof are disclosed. The compounds have activity in the gastroenteric system, particularly anti-ulcerogenic and gastric anti-secretory activity. Additionally, the compounds have activity in reducing the undesired gastrointestinal side-effects resulting from systemic administration of anti-inflammatory prostaglandin synthetase inhibitors.

10 Claims, No Drawings

SUBSTITUTED ETHENYL DERIVATIVES OF 1H-PYRAZOLO-[1,5-A]PYRIMIDINE HAVING GASTROENTERIC ACTIVITY, COMPOSITIONS THEREOF, AND METHODS OF USING THE SAME

DESCRIPTION

The present invention relates to new substituted ethenyl derivatives of 1H-pyrazolo[1,5-a]pyrimidine, to a process for their preparation and to pharmaceutical compositions containing them.

The invention provides compounds having the following general formula (I)

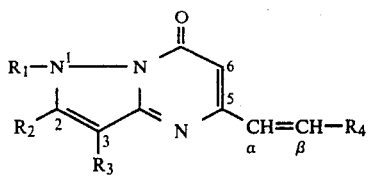

wherein
$R_1$ is:
(a) hydrogen or $C_1$-$C_6$ alkyl;
(b) a pyridyl group, unsubstituted or substituted by $C_1$-$C_6$ alkyl;
(c) a benzyl group, wherein the phenyl ring is unsubstituted or substituted by one or more substituents chosen from halogen, $C_1$-$C_6$ alkoxy and $C_1$-$C_6$ alkyl;
(d) a phenyl ring, unsubstituted or substituted by one or more substituents chosen from halogen, trihalo-$C_1$-$C_6$ alkyl, $C_1$-$C_6$ alkoxy, $C_1$-$C_6$ alkyl, formylamino, $C_2$-$C_6$ alkanoylamino, nitro and amino;
each of
$R_2$ and $R_3$ independently represents hydrogen, halogen or $C_1$-$C_6$ alkyl;
$R_4$ represents a pyridyl group, unsubstituted or substituted by $C_1$-$C_6$ alkyl;
and the pharmaceutically acceptable salts thereof.

The invention includes also the metabolites, the metabolic precursors of the compounds of formula (I) and all the possible isomers, e.g., cis or trans isomers and optical isomers, and the mixtures thereof. Preferably the —CH=CH-$R_4$ moiety, wherein $R_4$ is as defined above, is in the trans configuration.

The alkyl, alkoxy, trihalo-alkyl and alkanoylamino groups may be branched or straight chain groups. A halogen atom is for example chlorine, fluorine or bromine, preferably it is chlorine or fluorine. A $C_2$-$C_6$ alkanoylamino group is for example a group chosen from acetylamino, propionylamino, butyrylamino, valerylamino and isovalerylamino; preferably it is acetylamino or propionylamino.

A trihalo-$C_1$-$C_6$ alkyl group is, for example, a trifluoro-$C_1$-$C_6$ alkyl group, in particular it is trifluoro-$C_1$-$C_4$ alkyl, preferably trifluoromethyl.

When $R_1$ and/or $R_4$ is a pyridyl group substituted by a $C_1$-$C_6$ alkyl group, the alkyl group is, for example, methyl, ethyl or propyl; preferably, it is methyl. When $R_1$, is a benzyl ring substituted as defined above, the phenyl ring is preferably substituted by one or two substituents chosen from chlorine, fluorine, methyl and methoxy.

When $R_1$ is phenyl ring substituted as defined above, it is preferably substituted by one or two substituents chosen from chlorine, fluorine, amino, acetylamino, methyl and trifluoromethyl.

When $R_2$ and/or $R_3$ represents a $C_1$-$C_6$ alkyl group, it is, for example, methyl, ethyl, propyl and isopropyl, preferably it is methyl.

Preferred compounds of this invention are the compounds of formula (I), wherein
$R_1$ represents (a') pyridyl; (b') phenyl, unsubstituted or substituted by a substituent chosen from amino, acetylamino, methyl, chlorine, fluorine and trifluoromethyl; (c') benzyl or (d') $C_1$-$C_4$ alkyl;
each of $R_2$ and $R_3$, independently, represents hydrogen, chlorine or methyl;
$R_4$ represents pyridyl, unsubstituted or substituted by methyl; and the pharmaceutically acceptable salts thereof.

Examples of pharmaceutically acceptable salts are those with inorganic acids, e.g., hydrochloric, hydrobromic, nitric and sulphuric acids and those with organic acids, e.g., citric, tartaric, maleic, malic, fumaric, methanesulphonic and ethanesulphonic acids.

Examples of particularly preferred compounds of the invention are:
1-phenyl-5-trans-[2-(3-pyridyl)-ethenyl]-1H,7H-pyrazolo[1,5-a]pyrimidine-7-one;
1-(4-fluoro-phenyl)-5-trans-[2-(6-methyl-2-pyridyl)-ethenyl]-1H,7H-pyrazolo[1,5-a]pyrimidine-7-one;
1-(4-methyl-phenyl)-5-trans-[2-(3-pyridyl)-ethenyl]-1H,7H-pyrazolo[1,5-a]pyrimidine-7-one;
1-(4-methoxy-phenyl)-5-trans-[2-(3-pyridyl)-ethenyl]-1H,7H-pyrazolo[1,5-a]pyrimidine-7-one;
1-(4-fluoro-phenyl)-5-trans-[2-(3-pyridyl)-ethenyl]-1H,7H-pyrazolo[1,5-a]pyrimidine-7-one;
1-(4-chloro-phenyl)-5-trans-[2-(3-pyridyl)-ethenyl]-1H,7H-pyrazolo[1,5-a]pyrimidine-7-one;
1-(3-chloro-phenyl)-5-trans-[2-(3-pyridyl)-ethenyl]-1H,7H-pyrazolo[1,5-a]pyrimidine-7-one;
1-(3-trifluoromethyl-phenyl)-5-trans-[2-(3-pyridyl)-ethenyl]-1H,7H-pyrazolo[1,5-a]pyrimidine-7-one;
1-phenyl-5-trans-[2-(6-methyl-2-pyridyl)-ethenyl]-1H,7H-pyrazolo[1,5-a]pyrimidine-7-one;
1-phenyl-5-trans-[2-(4-pyridyl)-ethenyl]-1H,7H-pyrazolo[1,5-a]pyrimidine-7-one;
1-(4-acetylamino-phenyl)-5-trans-[2-(3-pyridyl)-ethenyl]-1H,7H-pyrazolo[1,5-a]pyrimidine-7-one;
1-(4-amino-phenyl)-5-trans-[2-(3-pyridyl)-ethenyl]-1H,7H-pyrazolo[1,5-a]pyrimidine-7-one;
3-methyl-1-phenyl-5-trans-[2-(3-pyridyl)-ethenyl]-1H,7H-pyrazolo[1,5-a]pyrimidine-7-one; and
1-phenyl-5-trans-[2-(2-pyridyl)-ethenyl]-1H,7H-pyrazolo[1,5-a]pyrimidine-7-one,
and the pharmaceutically acceptable salts thereof, in particular the hydrochlorides and the methanesulphonates.

The compounds of the invention are prepared, for example, by a process comprising
(A) reacting a compound of formula (II)

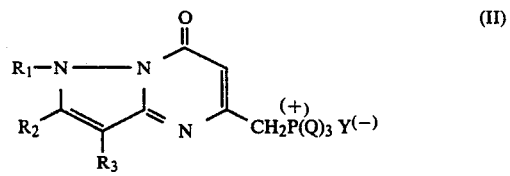

wherein $R_1$, $R_2$ and $R_3$ are as defined above, Q is aryl or $C_1$-$C_6$ alkyl, and $Y^{(-)}$ represents an acidic anion, with an aldehyde of formula (III)

$$R_4\text{—CHO} \qquad (III)$$

wherein $R_4$ is as defined above; or (B) reacting a compound of formula (IV)

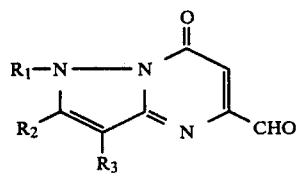
(IV)

wherein $R_1$, $R_2$ and $R_3$ are as defined above, with a compound of formula (V)

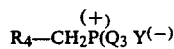
(V)

wherein $R_4$, Q and $Y^{(-)}$ are as defined above, or alternatively with a compound of formula (VI)

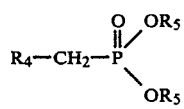
(VI)

wherein $R_4$ is as defined above and $R_5$ is $C_1$-$C_4$ alkyl; and, if desired, converting a compound of formula (I) into another compound of formula (I) and/or if desired, converting a compound of formula (I) into a pharmaceutically acceptable salt and/or, if desired, obtaining a free compound of formula (I) from a salt thereof and/or if desired, separating a mixture of isomers into the single isomers.

The acidic anion $Y^{(-)}$ in the compounds of formula (II) and (V) is, for example, an acidic anion deriving from a hydrohalic acid, preferably deriving from hydrochloric or hydrobromic acid.

When Q in the compounds of formula (II) and (V) is aryl, it is preferably phenyl; and when Q is $C_1$-$C_6$ alkyl, it is preferably ethyl.

The reaction between a compound of formula (II) and an aldehyde of formula (III) as well as the reaction of a compound of formula (IV) with a compound of formula (V) or with a compound of formula (VI), may, for example, be carried out by treatment with a base such as dimethylsulphinyl carbanion or sodium methoxide or sodium hydride or potassium terbutoxide or with an alkyllithium or an aryllithium derivative, preferably with methyllithium or butyllithium or phenyllithium, in an organic solvent such as dichloromethane, dichloroethane, benzene, toluene, tetrahydrofuran, dimethylsulfoxide, dimethylformamide, dimethylacetamide or their mixtures at a temperature varying from about 0° C. to about 100° C.

A compound of formula (I) may be converted, as stated above, into another compound of formula (I) by known methods; for example, an amino group as substituent in a phenyl ring in a compound of formula (I) may be converted into a formylamino or a $C_2$-$C_6$ alkanoylamino group using conventional methods well known in organic chemistry.

A nitro group as substituent in a phenyl ring in a compound of formula (I) may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active acid and subsequent fractional crystallization.

Thus, the separation of a mixture of geometric isomers may be carried out, for example, by fractional crystallization.

The compounds of formula (II) may be prepared, for example, by reacting a compound of formula (VII)

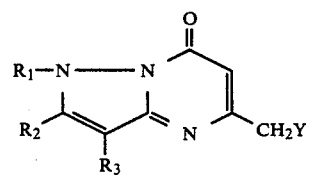
(VII)

wherein Y is a radical capable of being converted into an anion $Y^{(-)}$ as defined above and $R_1$, $R_2$ and $R_3$ are as defined above, with a compound of formula $PQ_3$, wherein Q is as defined above, in a solvent such as, benzene, toluene, xylene or acetonitrile at a temperature varying between room temperature and the reflux temperature.

The compounds of formula (IV) may be prepared, for example, by oxidizing a compound of formula (VIII)

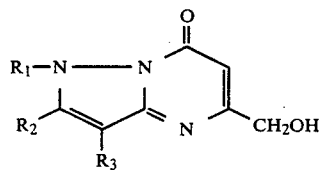
(VIII)

wherein $R_1$, $R_2$ and $R_3$ are as defined above, for example, with dimethylsulfoxide in the presence of dicyclohexylcarbodiimide and phosphoric acid or pyridiniumtrifluoroacetate (Moffat reaction) in a solvent such as benzene, toluene or dimethylsulfoxide at a temperature varying between 0° C. and about 50° C.

The compounds of formula (VII) wherein Y is halogen may, for example, be prepared by reacting a compound of formula (IX)

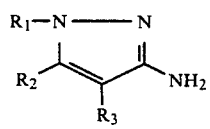
(IX)

wherein $R_1$, $R_2$ and $R_3$ are as defined above, with a compound of formula (X)

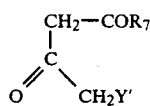

wherein $R_7$ is $C_1$-$C_6$ alkoxy and Y' represents a halogen atom, preferably chlorine.

The reaction between a compound of formula (IX) and a compound of formula (X) may, for example, be carried out in the presence of an acid condensing agent such as polyphosphoric acid (polyphosphoric acid means a mixture of about equal weights of 99% $H_3PO_4$ and $P_2O_5$), sulphuric acid, methanesulphonic acid or p-toluenesulphonic acid, at a temperature ranging preferably between about 50° C. and 150° C.; the reaction may be carried out in an organic solvent such as, dimethylformamide, dimethylacetamide, acetic acid, formic acid, benzene, toluene, xylene, ethylene glycol monomethylether or dichloroethane, but it is preferably carried out in the absence of a solvent.

The compounds of formula (VIII) may be prepared, for example, by reacting a compound of formula (VII) wherein Y is a good leaving group, for example, Cl or Br, with potassium or sodium acetate in dimethylformamide at a temperature varying between room temperature and about 100° C., so obtaining the corresponding acetoxy-derivative, which in turn is hydrolysed to the corresponding alcohol (VIII), for example, by treatment with 37% HCl in dioxane at a temperature varying between room temperature and the reflux temperature.

The compounds of formula (III), (V), (VI), (IX) and (X) are known compounds and may be prepared by conventional methods: in some cases they are commercially available products.

The compounds of the present invention are active on the gastroenteric system, in particular they are endowed with anti-ulcerogenic and gastric anti-secretory activity and are therefore useful in therapy, for example in the prevention and treatment of peptic, e.g. duodenal, gastric and exophageal, ulcers and to inhibit gastric acid secretion. The compounds of the invention are also useful for reducing the undesirable gastrointestinal sideeffects resulting from systemic administration of antiinflammatory prostaglandin synthetase inhibitors and may be, therefore, used for this purpose in association with them. The anti-ulcerogenic activity of the compounds of the invention is shown, e.g., by the fact that they are active in the test of the inhibition of restraint ulcers in rats, according to the method of Bonfils et al., (Th/érapie, 1960, 15, 1096; Jap. J. Pharmac. 1968, 18, 9). Six Sprague-Dawley male rats (100–120 g) fasted 24 hours were used for the experiment: a square flexible small-mesh were netting was used for the immobilization and 4 hours after the immobilization the rats were sacrificed, their stomachs were removed and the lesions counted under a dissecting microscope. The tested compounds were administered per os (p.o.) one hour before the immobilization. The compounds of the invention own also gastric antisecretory activity as shown, e.g., by the fact that they proved to be active, after intraduodenal administration, in inhibiting the gastric secretion in rats according to the method of H. Shay et al. (Gastroenter., 1945, 43, 5). Gastric antisecretory activity was evaluated in rats by the pylorus ligature technique. Six Sprague-Dawley male rats (110–130 g) were used for each group. Twenty-four hours before the test, the rats were deprived of food but their water supply was mantained. On the day of the operation, the pylorus was ligated under light ether anaesthesia. Each compound was injected intraduodenally (i.d.) at the time of the ligature. Four hours after the ligature the rats were sacrificed, the stomach secretion was collected and centrifuged at 3500 r.p.m. for 10 minutes, and the volume, less sediment, was determined.

The amount of the free hydrochloric acid in the gastric juice was determined by titration against 0.01N sodium hydroxide to pH 7.0 on the pH-meter.

The following Table shows, for example, the approximate $ED_{50}$ values of the anti-ulcerogenic activity and the gastric antisecretory activity in the rat obtained for one of the compounds of this invention: 1-phenyl-5-trans-[2-(3-pyridyl)-ethenyl]-1H,7H-pyrazolo[1,5-a]pyrimidine-7-one, identified by the internal code FCE 21542:

TABLE

| Compound | Antiulcerogenic activity $ED_{50}$ p.o. | Gastric antisecretory activity $ED_{50}$ i.d. |
| --- | --- | --- |
| FCE 21542 | 7 mg/kg | 3.2 mg/kg |

In view of their high therapeutic index, the compounds of the invention can be used safely in medicine. For example, the approximate acute toxicity ($LD_{50}$) of the compound 1-phenyl-5-trans-[2-(3-pyridyl)-ethenyl]-1H,7H-pyrazolo [1,5-a]pyrimidine-7-one (FCE 21542) in the mouse, determined by single administration of increasing doses and measured on the seventh day after the day of treatment, is higher than 400 mg/kg per os. Analogous toxicity data have been found for other compounds of the invention. The compounds of the invention can be administered in a variety of dosage forms, e.g. orally, in the form of tablets, capsules, sugar or film coated tablets, liquid solutions or suspensions, rectally, in the form of suppositories, parenterally, e.g. intramuscularly, or by intravenous injection or infusion. The dosage depends on the age, weight, conditions of the patient and administration route; for example the dosage adopted for oral administration to adult humans may range from about 50 to about 200 mg pro dose, from 1 to 5 times daily. The invention includes also pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. The following examples illustrate but do not limit the invention.

EXAMPLE 1

3-amino-1-phenyl-pyrazole (4 g) was reacted with ethyl 4-chloro-acetoacetate (4.1 g) in polyphosphoric acid (19.8 g; 10.6 g of $H_3PO_4$ and 9.2 g of $P_2O_5$) under stirring at 100° C. for 30 minutes: after cooling the reaction mixture was diluted with ice water and neutralized with 35% NaOH. The precipitate was filtered and washed with water to give 5-chloromethyl-1-phenyl-1H,7H-pyrazolo[1,5-a]pyrimidine-7-one, m.p. 194°–196° C. (5.9 g), which was reacted with triphenylphosphine (6.75 g) in acetonitrile (190 ml) at reflux temperature for 65 hours. After cooling the solution was evaporated in vacuo to dryness and the residue was treated with ethyl acetate: filtration of the crystalline product gave (1-phenyl-1H,7H-pyrazolo[1,5-a]pyrimidine-7-one-5-yl)-methyl-triphenylphosphonium chloride, m.p. 245°–247° C. (10 g), which was dissolved in chloroform (100 ml) and added dropwise to a suspension of 75% NaH (0.74 g) in chloroform (50 ml) and dimethylsulphoxide (5 ml) mantaining the temperature under 20° C.

The reaction mixture was kept 1 hour under stirring at room temperature, then 3-pyridine-carboxaldehyde (2.25 g) dissolved in chloroform (5 ml) was added and the mixture was allowed to react at room temperature for 30 minutes. After dilution with ice water and neutralization with $NaH_2PO_4$ the organic phase was separated and evaporated in vacuo to dryness: crystallization from isopropyl alcohol gave 2.55 g of 1-phenyl-5-trans-[2-(3-pyridyl)ethenyl]-1H,7H-pyrazolo[1,5-a]pyrimidine-7-one, m.p. 221°–224° C., N.M.R. (CDCl$_3$) δ p.p.m.: 6.19 (s) (1H, C-6 proton), 6.59 (d) (1H, C-3 proton), 7.08 (d) (1H, β-ethenylproton), 7.22–7.62 (m) (6H, phenyl protons and C-5 pyridyl proton), 7.76 (d) (1H, C-2 proton), 7.78 (d) (1H, α-ethenyl proton), 7.93 (dt) (1H, C-4 pyridyl proton), 8.58 (dd) (1H, C-6 pyridyl proton), 8.83 (d) (1H, C-2 pyridyl proton); $J_{H\alpha H\beta} = 16$ Hz.

By proceeding analogously the following compounds were prepared:

1-(4-methyl-phenyl)-5-trans-[2-(3-pyridyl)-ethenyl]-1H,7H-pyrazolo[1,5-a]pyrimidine-7-one, m.p. 230°–235° C. dec.;

1-(3-methyl-phenyl)-5-trans-[2-(3-pyridyl)-ethenyl]-1H,7H-pyrazolo[1,5-a]pyrimidine-7-one;

1-(2-methyl-phenyl)-5-trans-[2-(3-pyridyl)-ethenyl]-1H,7H-pyrazolo[1,5-a]pyrimidine-7-one;

1-(4-methoxy-phenyl)-5-trans-[2-(3-pyridyl)-ethenyl]-1H,7H-pyrazolo[1,5-a]pyrimidine-7-one;

1-(3-methoxy-phenyl)-5-trans-[2-(3-pyridyl)-ethenyl]-1H,7H-pyrazolo[1,5-a]pyrimidine-7-one;

1-(2-methoxy-phenyl)-5-trans-[2-(3-pyridyl)-ethenyl]-1H,7H-pyrazolo[1,5-a]pyrimidine-7-one;

1-(2-nitro-phenyl)-5-trans-[2-(3-pyridyl)-ethenyl]-1H,7H-pyrazolo[1,5-a]pyrimidine-7-one;

1-(4-fluoro-phenyl)-5-trans-[2-(3-pyridyl)-ethenyl]-1H,7H-pyrazolo[1,5-a]pyrimidine-7-one, m.p. 208°–209° C.;

1-(4-chloro-phenyl)-5-trans-[2-(3-pyridyl)-ethenyl]-1H,7H-pyrazolo[1,5-a]pyrimidine-7-one, m.p. 225°–228° C. dec.;

1-(3-chloro-phenyl)-5-trans-[2-(3-pyridyl)-ethenyl]-1H,7H-pyrazolo[1,5-a]pyrimidine-7-one, m.p. 199°–201° C.;

1-(2-chloro-phenyl)-5-trans-[2-(3-pyridyl)-ethenyl]-1H,7H-pyrazolo[1,5-a]pyrimidine-7-one;

1-(4-nitro-phenyl)-5-trans-[2-(3-pyridyl)-ethenyl]-1H,7H-pyrazolo[1,5-a]pyrimidine-7-one, m.p. 240°–247° C. dec.;

1-(3-nitro-phenyl)-5-trans-[2-(3-pyridyl)-ethenyl]-1H,7H-pyrazolo[1,5-a]pyrimidine-7-one;

1-(3-trifluoromethyl-phenyl)-5-trans-[2-(3-pyridyl)ethenyl]-1H,7H-pyrazolo[1,5-a]pyrimidine-7-one;

3-methyl-1-phenyl-5-trans-[2-(3-pyridyl)-ethenyl]-1H,7H-pyrazolo[1,5-a]pyrimidine-7-one, m.p. 240°–242° C.;

3-methyl-1-(4-methyl-phenyl)-5-trans-[2-(3-pyridyl)-ethenyl]-1H,7H-pyrazolo[1,5-a]pyrimidine-7-one;

3-methyl-1-(3-trifluoromethyl-phenyl)-5-trans-[2-(3-pyridyl)-ethenyl]-1H,7H-pyrazolo[1,5-a]pyrimidine-7-one;

3-methyl-1-(4-nitro-phenyl)-5-trans-[2-(3-pyridyl)-ethenyl]-1H,7H-pyrazolo[1,5-a]pyrimidine-7-one;

1-(4-fluoro-phenyl)-3-methyl-5-trans-[2-(3-pyridyl)-ethenyl]-1H,7H-pyrazolo[1,5-a]pyrimidine-7-one;

1-(4-chloro-phenyl)-3-methyl-5-trans-[2-(3-pyridyl)-ethenyl]-1H,7H-pyrazolo[1,5-a]pyrimidine-7-one;

1-(3-chloro-phenyl)-3-methyl-5-trans-[2-(3-pyridyl)-ethenyl]-1H,7H-pyrazolo[1,5-a]pyrimidine-7-one;

2-chloro-1-phenyl-5-trans-[2-(3-pyridyl)-ethenyl]-1H,7H-pyrazolo[1,5-a]pyrimidine-7-one, m.p. 213°–214° C.;

2-chloro-1-(4-methyl-phenyl)-5-trans-[2-(3-pyridyl)-ethenyl]-1H,7H-pyrazolo[1,5-a]pyrimidine-7-one;

2-chloro-1-(4-nitro-phenyl)-5-trans-[2-(3-pyridyl)-ethenyl]-1H,7H-pyrazolo[1,5-a]pyrimidine-7-one;

2-chloro-1-(4-fluoro-phenyl)-B 5-trans-[2-(3-pyridyl)-ethenyl]-1H,7H-pyrazolo[1,5-a]pyrimidine-7-one;

2-chloro-1-(4-chloro-phenyl)-5-trans-[2-(3-pyridyl)-ethenyl]-1H,7H-pyrazolo[1,5-a]pyrimidine-7-one;

2-chloro-1-(3-chloro-phenyl)-5-trans-[2-(3-pyridyl)-ethenyl]-1H,7H-pyrazolo[1,5-a]pyrimidine-7-one;

2-chloro-1-(3-trifluoromethyl-phenyl)-5-trans-[2-(3-pyridyl)-ethenyl]-1H,7H-pyrazolo[1,5-a]pyrimidine-7-one;

2-methyl-1-phenyl-5-trans-[2-(3-pyridyl)-ethenyl]-1H,7H-pyrazolo[1,5-a]pyrimidine-7-one;
2-methyl-1-(4-methyl-phenyl)-5-trans-[2-(3-pyridyl)ethenyl]-1H,7H-pyrazolo[1,5-a]pyrimidine-7-one;
2-methyl-1-(4-nitro-phenyl)-5-trans-[2-(3-pyridyl)-ethenyl]-1H,7H-pyrazolo[1,5-a]pyrimidine-7-one;
1-(4-fluoro-phenyl)-2-methyl-5-trans-[2-(3-pyridyl)-ethenyl]-1H,7H-pyrazolo[1,5-a]pyrimidine-7-one;
1-(4-chloro-phenyl)-2-methyl-5-trans-[2-(3-pyridyl)-ethenyl]-1H,7H-pyrazolo[1,5-a]pyrimidine-7-one;
1-(3-chloro-phenyl)-2-methyl-5-trans-[2-(3-pyridyl)-ethenyl]-1H,7H-pyrazolo[1,5-a]pyrimidine-7-one;
1-(2,4-dichloro-phenyl)-5-trans-[2-(3-pyridyl)-ethenyl]-1H,7H-pyrazolo[1,5-a]pyrimidine-7-one;
1-(3,4-dichloro-phenyl)-5-trans-[2-(3-pyridyl)-ethenyl]-1H,7H-pyrazolo[1,5-a]pyrimidine-7-one;
1-(3,5-dichloro-phenyl)-5-trans-[2-(3-pyridyl)-ethenyl]-1H,7H-pyrazolo[1,5-a]pyrimidine-7-one;
1-(2,5-dichloro-phenyl)-5-trans-[2-(3-pyridyl)-ethenyl]-1H,7H-pyrazolo[1,5-a]pyrimidine-7-one;
1-(3,4-dichloro-phenyl)-2-methyl-5-trans-[2-(3-pyridyl)-ethenyl]-1H,7H-pyrazolo[1,5-a]pyrimidine-7-one;
1-(2,4-dichloro-phenyl)-2-methyl-5-trans-[2-(3-pyridyl)-ethenyl]-1H,7H-pyrazolo[1,5-a]pyrimidine-7-one;
1-(4-bromo-phenyl)-5-trans-[2-(3-pyridyl)-ethenyl]-1H,7H-pyrazolo[1,5-a]pyrimidine-7-one;
1-(2,4-dichloro-phenyl)-3-methyl-5-trans-[2-(3-pyridyl)-ethenyl]-1H,7H-pyrazolo[1,5-a]pyrimidine-7-one;
1-(3,4-dichloro-phenyl)-3-methyl-5-trans-[2-(3-pyridyl)-ethenyl]-1H,7H-pyrazolo[1,5-]pyrimidine-7-one;
1-(3,5-dichloro-phenyl)-3-methyl-5-trans-[2-(3-pyridyl)-ethenyl]-1H,7H-pyrazolo[1,5-a]pyrimidine-7-one; and
1-(2,5-dichloro-phenyl)-3-methyl-5-trans-[2-(3-pyridyl)-ethenyl]-1H,7H-pyrazolo[1,5-a]pyrimidine-7-one.

EXAMPLE 2

By proceeding according to Example 1, using suitable pyridine-carboxaldehydes, the following compounds were prepared:
1-phenyl-5-trans-[2-(2-pyridyl)-ethenyl]-1H,7H-pyrazolo [1,5-a]pyrimidine-7-one, m.p. 255°-257° C.;
1-phenyl-5-trans-[2-(4-pyridyl)-ethenyl]-1H,7H-pyrazolo [1,5-a]pyrimidine-7-one, m.p. 250°-255° C. (dec.);
1-phenyl-5-trans-[2-(6-methyl-2-pyridyl)-ethenyl]-1H,7H-pyrazolo[1,5-a]pyrimidine-7-one, m.p. 228°-232° C. (dec.);
3-methyl-1-phenyl-5-trans-[2-(2-pyridyl)-ethenyl]-1H,7H-pyrazolo[1,5-a]pyrimidine-7-one;
3-methyl-1-phenyl-5-trans-[2-(6-methyl-2-pyridyl)ethenyl]-1H,7H-pyrazolo[1,5-a]pyrimidine-7-one;
1-(4-fluoro-phenyl)-5-trans-[2-(6-methyl-2-pyridyl)-ethenyl]-1H,7H-pyrazolo[1,5-a]pyrimidine-7-one;
2-methyl-1-phenyl-5-trans-[2-(6-methyl-2-pyridyl)-ethenyl]-1H,7H-pyrazolo[1,5-a]pyrimidine-7-one;
1-(4-chloro-phenyl)-5-trans-[2-(6-methyl-2-pyridyl)-ethenyl]-1H,7H-pyrazolo[1,5-a]pyrimidine-7-one;
1-(3-chloro-phenyl)-5-trans-[2-(6-methyl-2-pyridyl)-ethenyl]-1H,7H-pyrazolo[1,5-a]pyrimidine-7-one; and
1-(4-methyl-phenyl)-5-trans-[2-(6-methyl-2-pyridyl)-ethenyl]-1H,7H-pyrazolo[1,5-a]pyrimidine-7-one.

EXAMPLE 3

By proceeding according to Example 1, starting from suitable 3-amino-1-pyridyl-pyrazoles, the following compounds were prepared:
1-(3-pyridyl)-5-trans-[2-(2-pyridyl)-ethenyl]-1H,7H-pyrazolo[1,5-a]pyrimidine-7-one;
1-(3-pyridyl)-5-trans-[2-(3-pyridyl)-ethenyl]-1H,7H-pyrazolo[1,5-a]pyrimidine-7-one;
1-(2-pyridyl)-5-trans-[2-(3-pyridyl)-ethenyl]-1H,7H-pyrazolo[1,5-a]pyrimidine-7-one, m.p. 219°-221° C.;
2-methyl-1-(3-pyridyl)-5-trans-[2-(3-pyridyl)-ethenyl]-1H,7H-pyrazolo[1,5-a]pyrimidine-7-one;
3-methyl-1-(3-pyridyl)-5-trans-[2-(3-pyridyl)-ethenyl]-1H,7H-pyrazolo[1,5-a]pyrimidine-7-one;
1-(3-pyridyl)-5-trans-[2-(6-methyl-2-pyridyl)-ethenyl]-1H,7H-pyrazolo[1,5-a]pyrimidine-7-one; and
3-methyl-1-(3-pyridyl)-5-trans-[2-(6-methyl-2-pyridyl)ethenyl]-1H,7H-pyrazolo[1,5-a]pyrimidine-7-one.

EXAMPLE 4

By proceeding according to Example 1, starting from suitable 3-amino-pyrazoles, the following compounds were prepared:
5-trans-[2-(3-pyridyl)-ethenyl]-1H,7H-pyrazolo[1,5-a]pyrimidine-7-one;
1-methyl-5-trans[2-(3-pyridyl)-ethenyl]-1H,7H-pyrazolo [1,5-a]pyrimidine-7-one, m.p. 203°-205° C.;
1-tert.butyl-5-trans-[2-(3-pyridyl)-ethenyl]-1H,7H-pyrazolo[1,5-a]pyrimidine-7-one;
1-benzyl-5-trans-[2-(3-pyridyl)-ethenyl]-1H,7H-pyrazolo [1,5-a]pyrimidine-7-one, m.p. 173°-175° C. (dec.);
1-(4-chloro-benzyl)-5-trans-[2-(3-pyridyl)-ethenyl]-1H,7H-pyrazolo[1,5-a]pyrimidine-7-one;
1-(4-fluoro-benzyl)-5-trans-[2-(3-pyridyl)-ethenyl]-1H,7H-pyrazolo[1,5-a]pyrimidine-7-one;
1-(3-methoxy-benzyl)-5-trans-[2-(3-pyridyl)-ethenyl]-1H,7H-pyrazolo[1,5-a]pyrimidine-7-one;
1-(4-methyl-benzyl)-5-trans-[2-(3-pyridyl)-ethenyl]-1H,7H-pyrazolo[1,5-a]pyrimidine-7-one;
1-benzyl-5-trans-[2-(6-methyl-2-pyridyl)-ethenyl]-1H,7H-pyrazolo[1,5-a]pyrimidine-7-one;
1-benzyl-2-methyl-5-trans-[2-(3-pyridyl)-ethenyl]-1H,7H-pyrazolo[1,5-a]pyrimidine-7-one;
1-benzyl-3-methyl-5-trans-[2-(3-pyridyl)-ethenyl]-1H,7H-pyrazolo[1,5-a]pyrimidine-7-one; and
1-tert.butyl-3-methyl-5-trans-[2-(3-pyridyl)-ethenyl]-1H,7H-pyrazolo[1,5-a]pyrimidine-7-one.

EXAMPLE 5

1-(4-nitro-phenyl)-5-trans-[2-(3-pyridyl)-ethenyl]-1H,7H-pyrazolo[1,5-a]pyrimidine-7-one, (5.2 g), was reacted with $SnCl_2.2H_2O$ (32.7 g) in 37% HCl (30 ml) and acetic acid (100 ml) under stirring at 60° C. for 1 hour. After cooling the precipitate was filtered and washed with water and then suspended under stirring in 2N NaOH: the product was filtered, washed with water until neutral and then purified over a $SiO_2$ column using chloroform: methanol 95:5 as eluent. Washings with isopropyl ether of the recovered product gave 2.6 g of 1-(4-amino-phenyl)-5-trans-[2-(3-pyridyl)-ethenyl]-1H,7H-pyrazolo[1,5-a] pyrimidine-7-one, m.p. 245°-250° C. dec., NMR (DMSO $d_6$)$\delta$ p.p.m.: 5.46 (bs) (2H, $NH_2$), 6.05 (s) (1H, C-6 proton), 6.56 (d) (2H, C-3 and C-5 phenyl protons), 6.62 (d) (1H, C-3 proton), 7.09 (d) (2H, C-2 and C-6 phenyl protons), 7.25 (d) (1H, $\beta$-ethenyl proton), 7.42 (dd) (1H, C-5 pyridyl proton), 7.72 (d) (1H, $\alpha$-ethenyl proton), 8.11 (dt) (1H, C-4 pyridyl proton), 8.28 (d) (1H, C-2 proton), 8.51 (dd) (1H, C-6 pyridyl proton), 8.82 (d) (1H, C-2 pyridyl proton); $J_{H\alpha H\beta}=16$ Hz.

By proceeding analogously the following compounds were prepared:

1-(3-amino-phenyl)-5-trans-[2-(3-pyridyl)-ethenyl]-1H,7H-pyrazolo[1,5-a]pyrimidine-7-one;

1-(4-amino-phenyl)-5-trans-[2-(2-pyridyl)-ethenyl]-1H,7H-pyrazolo[1,5-a]pyrimidine-7-one;

1-(4-amino-phenyl)-2-methyl-5-trans-[2-(3-pyridyl)ethenyl]-1H,7H-pyrazolo[1,5-a]pyrimidine-7-one;

1-(4-amino-phenyl)-3-methyl-5-trans-[2-(3-pyridyl)ethenyl]-1H,7H-pyrazolo[1,5-a]pyrimidine-7-one;

1-(4-amino-phenyl)-2-chloro-5-trans-[2-(3-pyridyl)ethenyl]-1H,7H-pyrazolo[1,5-a]pyrimidine-7-one;

1-(4-amino-phenyl)-5-trans-[2-(6-methyl-2-pyridyl)ethenyl]-1H,7H-pyrazolo[1,5-a]pyrimidine-7-one;

1-(3-amino-phenyl)-2-methyl-5-trans-[2-(3-pyridyl)-ethenyl]-1H,7H-pyrazolo[1,5-a]pyrimidine-7-one; and 1-(3-amino-phenyl)-3-methyl-5-trans-[2-(3-pyridyl)-ethenyl]-1H,7H-pyrazolo[1,5-a]pyrimidine-7-one.

EXAMPLE 6

1-(4-amino-phenyl)-5-trans-[2-(3-pyridyl)-ethenyl]-1H,7H-pyrazolo[1,5-a]pyrimidine-7-one (1 g), was reacted with acetic anhydride (3 ml) in pyridine (4 ml) and dimethylformamide (15 ml) at 60° C. for 3 hours. Dilution with ice water gave a precipitate, which was filtered and washed with water: crystallization from dimethylformamide-ethanol gave 0.85 g of 1-(4-acetylamino-phenyl)-5-trans-[2-(3-pyridyl)-ethenyl]-1H,7H-pyrazolo[1,5-a]pyrimidine-7-one, m.p. 270°-275° C. (dec.).

By proceeding analogously the following compounds were prepared:

1-(3-acetylamino-phenyl)-5-trans-[2-(3-pyridyl)-ethenyl]-1H-pyrazolo[1,5-a]pyrimidine-7-one;

1-(4-acetylamino-phenyl)-5-trans-[2-(2-pyridyl)-ethenyl]-1H,7H-pyrazolo[1,5-a]pyrimidine-7-one;

1-(4-acetylamino-phenyl)-2-methyl-5-trans-[2-(3-pyridyl)ethenyl]-1H,7H-pyrazolo[1,5-a]pyrimidine-7-one;

1-(4-acetylamino-phenyl)-3-methyl-5-trans-[2-(3-pyridyl)ethenyl]-1H,7H-pyrazolo[1,5-a]pyrimidine-7-one;

1-(4-acetylamino-phenyl)-2-chloro-5-trans-[2-(3-pyridylethenyl]-1H,7H-pyrazolo[1,5-a]pyrimidine-7-one;

1-(4-acetylamino-phenyl)-5-trans-[2-(6-methyl-2-pyridyl)ethenyl]-1H,7H-pyrazolo[1,5-a]pyrimidine-7-one;

1-(3-acetylamino-phenyl)-2-methyl-5-trans-[2-(3-pyridyl)-ethenyl]-1H,7H-pyrazolo[1,5-a]pyrimidine-7-one; and 1-(3-acetylamino-phenyl)-3-methyl-5-trans-[2-(3-pyridyl)-ethenyl]-1H,7H-pyrazolo[1,5-a]pyrimidine-7-one.

EXAMPLE 7

5-chloromethyl-1-phenyl-1H,7H-pyrazolo[1,5-a]pyrimidine-7-one (5.2 g), prepared according to Example 1, was dissolved in dimethylformamide (30 ml) and reacted with anhydrous potassium acetate (4 g) under stirring at room temperature for 20 hours. After dilution with ice water the precipitate was filtered and washed with water to give 5-acetoxymethyl-1-phenyl-1H,7H-pyrazolo[1,5-a]pyrimidine-7-one, m.p. 172°-175° C., (4.9 g) which was hydrolized by treatment with 8% HCl (50 ml) under stirring at 90° C. for 30 minutes. The reaction mixture was neutralized with 35% NaOH and the precipitate was filtered and washed with water to give 5-hydroxymethyl-1-phenyl-1H,7H-pyrazolo[1,5-a]pyrimidine-7-one, m.p. 241°-242° C., (4.1 g), which was reacted with dicyclohexylcarbodiimide (8 g) in benzene (60 ml) and dimethylsulphoxide (15 ml) in the presence of trifluoroacetic acid (0.6 ml) and pyridine (1 ml) under stirring at room temperature for 20 hours. After treatment with oxalic acid bihydrate (1.8 g) at room temperature, the precipitate of dicyclohexylurea was filtered off and the organic solution was evaporated in vacuo to dryness: the residue was purified over a SiO$_2$ column using chloroform: ethyl acetate=95:5 as eluent. The 7-formyl-1-phenyl-1H,7H-pyrazolo[1,5-a]pyrimidine-7-one so obtained (2.5 g) was reacted with the ylide obtained by treatment of (3-pyridyl)-methyl-triphenylphosphonium chloride (4.2 g) with potassium tert-butoxide (1.25 g) in dimethylsulphoxide (20 ml) at room temperature for 30 minutes. After dilution with ice water the precipitate was filtered and washed with water: crystallization from isopropyl alcohol gave 2.05 g of 1-phenyl-5-trans-[2-(3-pyridyl)ethenyl]-1H,7H-pyrazolo[1,5-a]pyrimidine-7-one, m.p. 221°-224° C.

By proceeding analogously the following compounds were prepared:

1-(4-fluoro-phenyl)-5-trans-[2-(3-pyridyl)-ethenyl]-1H,7H-pyrazolo[1,5-a]pyrimidine-7-one, m.p. 208°-209° C.;

1-(4-chloro-phenyl)-5-trans-[2-(3-pyridyl)-ethenyl]-1H,7H-pyrazolo[1,5-a]pyrimidine-7-one, m.p. 225°-228° C. dec.;

1-(3-chloro-phenyl)-5-trans-[2-(3-pyridyl)-ethenyl]-1H,7H-pyrazolo[1,5-a]pyrimidine-7-one, m.p. 119°-201° C.;

1-(4-methyl-phenyl)-5-trans-[2-(3-pyridyl)-ethenyl]-1H,7H-pyrazolo[1,5-a]pyrimidine-7-one, m.p. 230°-235° C. dec.; and 3-methyl-1-phenyl-5-trans-[2-(3-pyridyl)-ethenyl]-1H,7H-pyrazolo[1,5-a]pyrimidine-7-one, m.p. 240°-242° C.

EXAMPLE 8

1-phenyl-5-trans-[2-(3-pyridyl)-ethenyl]-1H,7H-pyrazolo[1,5-a]pyrimidine-7-one (2 g) dissolved in ethyl acetate (200 ml) was treated with the stoichiometric amount of gaseous HCl at room temperature. The precipitate was filtered and washed with ethyl acetate to give 2. 1 g of 1-phenyl-5-trans-[2-(3-pyridyl)-ethenyl]-1H,7H-pyrazolo[1,5-a]pyrimidine-7-one, hydrochloride, m.p.>300° C.

By proceeding analogously the following compounds were prepared:

2-methyl-1-phenyl-5-trans-[2-(3-pyridyl)-ethenyl]-1H,7H-pyrazolo[1,5-a]pyrimidine-7-one, dihydrochloride, m.p. 257°-262° C. dec.;

1-(4-fluoro-phenyl)-5-trans-[2-(3-pyridyl)-ethenyl]-1H,7H-pyrazolo[1,5-a]pyrimidine-7-one, hydrochloride;

1-(4-chloro-phenyl)-5-trans-[2-(3-pyridyl)-ethenyl]-1H,7H-pyrazolo[1,5-a]pyrimidine-7-one, hydrochloride;

1-(3-chloro-phenyl)-5-trans-[2-(3-pyridyl)-ethenyl]-1H,7H-pyrazolo[1,5-a]pyrimidine-7-one, hydrochloride;

1-(4-methyl-phenyl)-5-trans-[2-(3-pyridyl)-ethenyl]-1H,7H-pyrazolo[1,5-a]pyrimidine-7-one, hydrochloride; and 3-methyl-1-phenyl-5-trans-[2-(3-pyridyl)-ethenyl]-1H,7H-pyrazolo[1,5-a]pyrimidine-7-one, hydrochloride.

EXAMPLE 9

Tablets, each weighing 150 mg and containing 50 mg of the active substance are manufactured as follows:

Compositions (for 10,000 tablets)

1-phenyl-5-trans-[2-(3-pyridyl)-ethenyl]-1H,7H-pyrazolo[1,5-a]pyrimidine-7-one: 500 g
Lactose: 710 g
Corn starch: 237.5 g
Talc powder: 37.5 g
Magnesium stearate: 15 g 1-phenyl-5-trans-[2-(3-pyridyl)-ethenyl]-1H,7H-pyrazolo[1,5-a]pyrimidine-7-one, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

We claim:

1. A compound of formula (I)

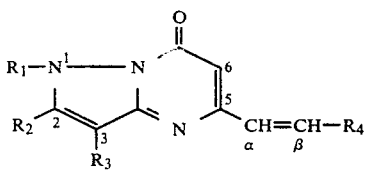

wherein
$R_1$ is:
(a) hydrogen or $C_1$–$C_6$ alkyl;
(b) an unsubstituted 2-pyridyl or 3-pyridyl group;
(c) a benzyl group, wherein the phenyl ring is unsubstituted or substituted by halogen, $C_1$–$C_6$ alkoxy or $C_1$–$C_6$ alkyl;
(d) a phenyl ring, unsubstituted or substituted by one or two groups chosen from halogen, trihalomethyl, $C_1$–$C_6$ alkoxy, $C_1$–$C_6$ alkyl, $C_2$–$C_6$ alkanoylamino, nitro and amino;
each of $R_2$ and $R_3$ independently represents hydrogen, halogen or $C_1$–$C_6$ alkyl;
$R_4$ represents a 2-pyridyl, 3-pyridyl or 4-pyridyl group, unsubstituted or substituted by $C_1$–$C_6$ alkyl;
or the pharmaceutically acceptable salts thereof.

2. A compound of formula (I), according to claim 1, wherein:
$R_1$ represents (a') 2-pyridyl or 3-pyridyl; (b') phenyl, unsubstituted or substituted by amino, acetylamino, methyl, chlorine, fluorine or trifluoromethyl; (c') benzyl or (d') $C_1$–$C_4$ alkyl;
each of $R_2$ and $R_3$, independently, represents hydrogen, chlorine or methyl;
$R_4$ represents 2-pyridyl, 3-pyridyl or 4-pyridyl, unsubstituted or substituted by methyl; or the pharmaceutically acceptable salts thereof.

3. A compound selected from the group consisting of:

1-phenyl-5-trans-[2-(3-pyridyl)-ethenyl]-1H,7H-pyrazolo[1,5-a]pyrimidine-7-one;
1-(4-fluoro-phenyl)-5-trans-[2-(6-methyl-2-pyridyl)ethenyl]-1H,7H-pyrazolo[1,5-a]pyrimidine-7-one;
1-(4-methyl-phenyl)-5-trans-[2-(3-pyridyl)-ethenyl]-1H,7H-pyrazolo[1,5-a]pyrimidine-7-one;
1-(4-methoxy-phenyl)-5-trans-[2-(3-pyridyl)-ethenyl]-1H,7H-pyrazolo[1,5-a]pyrimidine-7-one;
1-(4-fluoro-phenyl)-5-trans-[2-(3-pyridyl)-ethenyl]-1H,7H-pyrazolo[1,5-a]pyrimidine-7-one;
1-(4-chloro-phenyl)-5-trans-[2-(3-pyridyl)-ethenyl]-1H,7H-pyrazolo[1,5-a]pyrimidine-7-one;
1-(3-trifluoromethyl-phenyl)-5-trans-[2-(3-pyridyl)ethenyl]-1H,7H-pyrazolo[1,5-a]pyrimidine-7-one;
1-phenyl-5-trans-[2-(6-methyl-2-pyridyl)-ethenyl]-1H,7H-pyrazolo[1,5-a]pyrimidine-7-one;
1-phenyl-5-trans-[2-(4-pyridyl)-ethenyl]-1H,7H-pyrazolo[1,5-a]pyrimidine-7-one;
1-(4-acetylamino-phenyl)-5-trans-[2-(3-pyridyl)-ethenyl]-1H,7H-pyrazolo[1,5-a]pyrimidine-7-one;
1-(4-amino-phenyl)-5-trans-[2-(3-pyridyl)-ethenyl]-1H,7H-pyrazolo[1,5-a]pyrimidine-7-one;
3-methyl-1-phenyl-5-trans-[2-(3-pyridyl)-ethenyl]-1H,7H-pyrazolo[1,5-a]pyrimidine-7-one; and
1-phenyl-5-trans-[2-(2-pyridyl)-ethenyl]-1H,7H-pyrazolo[1,5-a]pyrimidine-7-one,
or the pharmaceutically acceptable salts thereof.

4. A pharmaceutical composition containing a suitable carrier and/or diluent and, as an active principle, a compound of formula (I) according to claim 1 or a pharmaceutically acceptable salt thereof.

5. A method of treating a human patient to reduce or eliminate the formation of gastrointestinal ulcers, to accelerate the healing process of ulcers present in the gastrointestinal tract, to reduce the undesirable gastrointestinal side effects resulting from systemic administration of antiinflammatory prostaglandin synthetase inhibitors, said method comprising administering to the patient an effective amount of the compound according to claim 1.

6. A method of treating a human patient to reduce or eliminate the formation of gastrointestinal ulcers, to accelerate the healing process of ulcers present in the gastrointestinal tract, to reduce the undesirable gastrointestinal side effects resulting from systemic administration of antiinflammatory prostaglandin synthetase inhibitors, said method comprising administering to the patient an effective amount of the pharmaceutical composition according to claim 4.

7. A method for the treatment of peptic ulcers in a patient comprising administering to the patient an antiulcerogenic effective amount of the compound according to claim 1.

8. A method for the treatment of excessive gastric secretion in a patient comprising administering to the patient a gastric anti-secretory effective amount of the compound according to claim 1.

9. A method for reducing the undesirable gastrointestinal side effects in a patient undergoing systemic administration of anti-inflammatory prostaglandin synthetase inhibitors comprising administering to the patient a therapeutically effective amount of the compound according to claim 1.

10. The compound 1-(3-chloro-phenyl)-5-trans-[2-(3-pyridyl)-ethenyl]-1H,7H-pyrazolo[1,5-a]pyrimidine-7-one; or the pharmaceutically acceptable salts thereof.

* * * * *